United States Patent [19]

Kumai et al.

[11] Patent Number: 5,241,111

[45] Date of Patent: Aug. 31, 1993

[54] PROCESSES FOR PRODUCING 5-FLUOROBENZOIC ACIDS AND THEIR INTERMEDIATES

[75] Inventors: Seisaku Kumai, Fujisawa; Masao Ohashi; Yutaka Yaginuma, both of Chigasaki; Katsuhiko Takeda, Fujisawa, all of Japan

[73] Assignees: Asahi Glass Company Ltd., Tokyo; Seimi Chemical Co., Ltd., Chigasaki, both of Japan

[21] Appl. No.: 614,598

[22] Filed: Nov. 15, 1990

[30] Foreign Application Priority Data

Nov. 17, 1989 [JP] Japan .................. 1-297609
Nov. 17, 1989 [JP] Japan .................. 1-297610

[51] Int. Cl.$^5$ ............................................. C07C 63/04
[52] U.S. Cl. ................................. 562/493; 558/318; 570/127
[58] Field of Search ..................................... 562/493

[56] References Cited

U.S. PATENT DOCUMENTS

3,187,057 6/1965 Pefer et al. ................. 562/493
4,439,620 3/1984 Klauce et al. .............. 562/493

FOREIGN PATENT DOCUMENTS

0164619 12/1985 European Pat. Off.
230947 8/1987 European Pat. Off.
0303291 2/1989 European Pat. Off.
1668068 7/1971 Fed. Rep. of Germany.
3142856 5/1983 Fed. Rep. of Germany.

OTHER PUBLICATIONS

CA 84(25):179843m 1970.
CA 90(1):6124y 1978.
Patent Abstracts of Japan, vol. 12, No. 467, (C-550) [3314], Dec. 7, 1988, & JP-A-63 188 643, Aug. 4, 1988, Y. Nishimura, et al., "Novel Fluorine-Containing Benzophenone and Production Thereof".
Chemical Abstracts, 77918q, vol. 113, No. 9, Aug. 27, 1990, & CN-A-1 031 074, Feb. 15, 1989, Y. Shi, et al., "Preparation of 2,4-Dichloro-5-Fluorobenzoic Acid".
Patent Abstracts of Japan, vol. 13, No. 205, (C-595) [3553], May 15, 1989, & JP-A-1 025 737, Jan. 27, 1989, S. Niizeki, et al., "Decarboxylation of Halogen-Substituted Benzenecarboxylic Acid".
Patent Abstracts of Japan, vol. 13, No. 187, (C-592) [3535], May 2, 1989, & JP-A-1 013 037, Jan. 17, 1989, Y. Yoshida, "Production of Aromatic Fluorine Compound".

Primary Examiner—Paul J. Killos
Attorney, Agent, or Firm—Oblon, Spivak, McClelland, Maier & Neustadt

[57] ABSTRACT

A process for producing a 5-fluorobenzoic acid of the formula (V), which comprises trichloromethylating a fluorobenzene of the formula (I) to obtain a 5-fluorobenzotrichloride of the formula (II), then reacting it with aqueous ammonia to obtain a 5-fluorobenzonitrile of the formula (III), reacting it with a fluorinating agent to obtain a 5-fluorobenzonitrile of the formula (IV) and hydrolyzing it:

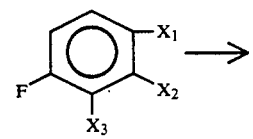

(I)

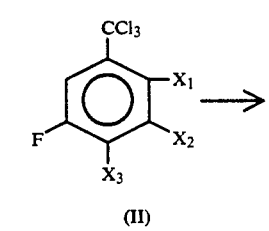

(II)

-continued
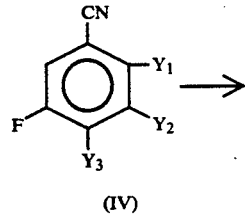
(IV)
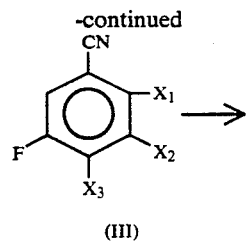
(III)
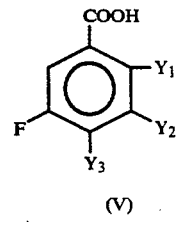
(V)
wherein each of $X_1$, $X_3$, $Y_1$ and $Y_3$ is a halogen atom, and each of $X_2$ and $Y_2$ is hydrogen or a halogen atom.
2 Claims, No Drawings

PROCESSES FOR PRODUCING 5-FLUOROBENZOIC ACIDS AND THEIR INTERMEDIATES

The present invention relates to processes for producing 5-fluorobenzoic acids useful as intermediates for medicines and their intermediates safely and simply on an industrial scale.

Heretofore, a trichloromethyl group has been considered to be a precursor for a carboxyl group. However, by the reaction of carbon tetrachloride with e.g. p-fluorobenzene (J. Yurmi et al., Yiyao Gongye, 16 (8), 370 (1985); CA, 104,50593 g) or o-difluorobenzene (Japanese Unexamined Patent Publication No. 188643/1988), a bisphenyldichloromethane is obtainable in good yield, and no substantial amount of benzotrichloride is obtainable.

However, 2,4-dichloro-5-fluorobenzotrichloride is obtainable by chlorinating 2,4-dichloro-5-fluorotoluene under irradiation with ultraviolet rays (Japanese Unexamined Patent Publication No. 74638/1983).

On the other hand, for the production of 2,4-dichloro-5-fluorobenzoic acid, it is known to employ a method of hydrolyzing 2,4-dichloro-5-fluorobenzotrichloride (Japanese Unexamined Patent Publication No. 74638/1983), a method of acetylating 1,3-dichloro-4-fluorobenzene, followed by haloformylation (EP 1760261 (1986); DE 3435392 (1986); Japanese Unexamined Patent Publication No. 85350/1986), or a method of reacting 1-bromo-2,4-dichloro-5-fluorobenzene with magnesium to obtain a Grignard reagent, which is then reacted with carbon dioxide (Japanese Unexamined Patent Publication No 237069/1985).

For the preparation of 2-chloro-4,5-difluorobenzoic acid, it is known to employ a method of hydrolyzing 2-chloro-4,5-difluorobenzotrifluoride (Japanese Unexamined Patent Publication No.108839/1987), or a method of acetylating 1-chloro-3,4-difluorobenzene, followed by haloformylation (Japanese Unexamined Patent Publication No. 45322/1989).

2-bromo-4,5-difluorobenzoic acid is obtained by hydrolyzing 2-bromo-4,5-difluorobenzonitrile (I. Cervena et al., Collect Czech Chem Commun., 42,2001 (1977); CA. 87, 201469e)

For the preparation of 2,4,5-trifluorobenzoic acid, it is known to employ a method of obtaining it at a low yield by the Balz-Schiemann reaction, or the Balz-Schiemann reaction and hydrolysis, of 2-amino-4,5-difluorobenzoic acid (G.C. Finger et al., Illinois State Geol. Survey Circ., 199,15 (1955)) or its ethyl ester (J. I. deGraw et at., J. Chem. Eng. Data, 13 (4), 587 (1968)), a method of reacting a Grignard reagent of 1-bromo-2,4,5-trifluorobenzene with carbon dioxide (Japanese Unexamined Patent Publications No. 160543/1983 and No. 188839/1983), a method of cyanating 1-bromo-2,4,5-trifluorobenzene, followed by hydrolysis (Japanese Unexamined Patent Publication No. 72885/1985; EP 191185 (1986)), a method of hydrolyzing a 2,4,5-trifluorobenzoic acid halide, a method of hydrolyzing 2,4,5-trifluorobenzotrifluoride (Japanese Unexamined Patent Publication No. 108839/1987) and a method of decarboxylating 3,4,6-trifluorophthalic acid (Japanese Unexamined Patent Publication No 52737/1989).

Further, for the preparation of 2,3,4-trichloro-5-fluorobenzoic acid, it is known to employ a method of nitrating 2,4-dichloro-5-fluorobenzoic acid to obtain 2,4-dichloro-5-fluoro-3-nitrobenzoic acid, followed by reduction and a Sandmeyer reaction (Japanese Unexamined Patent Publication No. 88157/1988).

As mentioned above, the conventional methods are not industrially advantageous involving irradiation with ultraviolet rays and the haloformylation reaction, Grignard reaction and Sandmeyer reaction with low batch efficiency and use of a diazonium salt or a hydrocyanic acid compound harmful to human bodies, as well as problems relating to the quality of the material.

It is an object of the present invention to solve the above mentioned drawbacks of the prior art.

The present invention provides a process for producing a 5-fluorobenzoic acid of the formula (V) useful as an intermediate for medicines and a 5-fluorobenzotrichloride of the formula (II) as an intermediate thereof, and a 5-fluorobenzonitrile of the formula (III), safely and simply on an industrial scale:

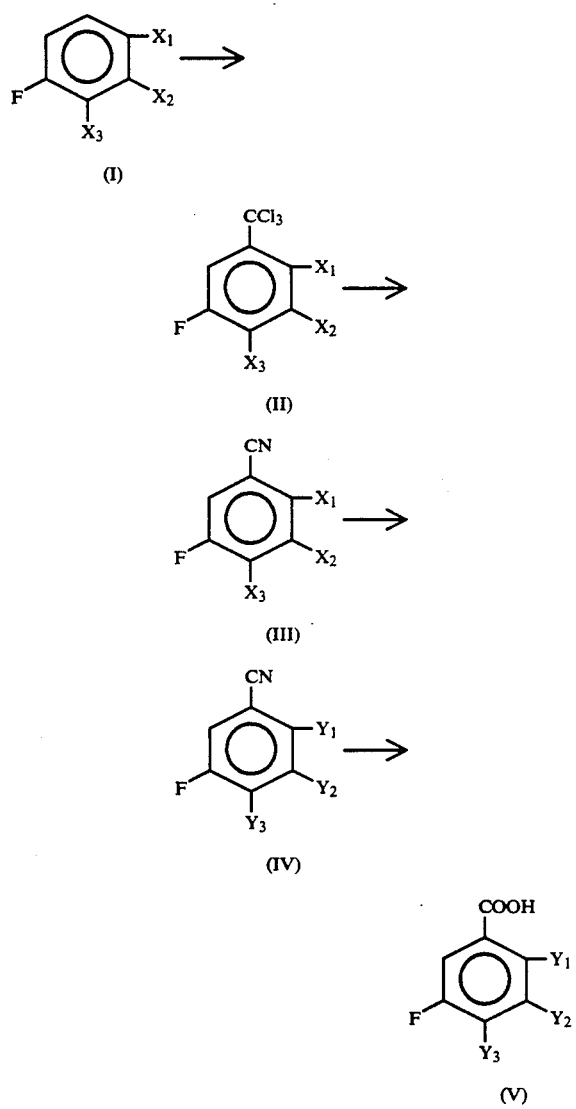

wherein each of $X_1$, $X_3$, $Y_1$ and $Y_3$ is a halogen atom, and each of $X_2$ and $Y_2$ is hydrogen or halogen atom.

The 5-fluorobenzoic acid of the formula (V) can be prepared by a process which comprises trichloromethylating a fluorobenzene of the formula (I) to obtain a 5-fluorobenzotrichloride of the formula (II), then reacting it with aqueous ammonia to obtain a 5-fluorobenzonitrile of the formula (III), reacting it with a fluorinating agent to obtain a 5-fluorobenzonitrile of the formula (IV) and hydrolyzing it, or a process which comprises reacting a fluorobenzene of the formula (I) with carbon tetrachloride in the presence of a Lewis acid catalyst to obtain a 5-fluorobenzotrichloride of the formula (II) and hydrolyzing it:

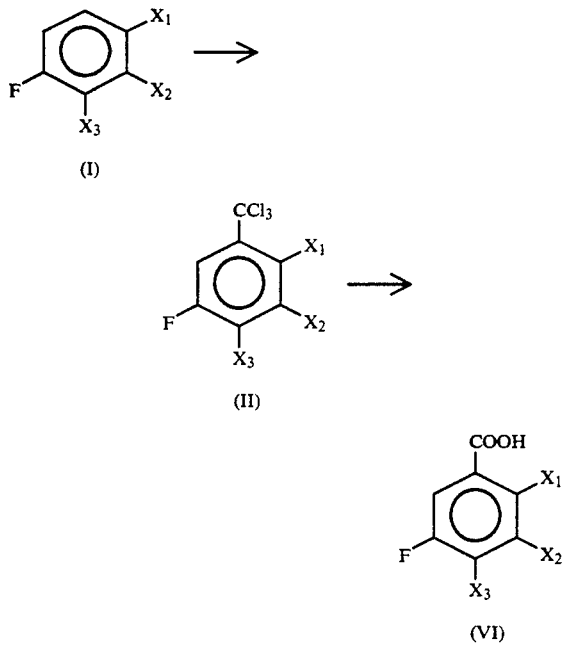

wherein each of $X_1$ and $X_3$ is a halogen atom, and $X_2$ is hydrogen or a halogen atom.

On the other hand, the 5-fluorobenzotrichloride of the formula (II) can be obtained by reacting a fluorobenzene of the formula (I) with carbon tetrachloride in the presence of a Lewis acid catalyst.

The 5-fluorobenzonitrile of the formula (III) can be prepared by trichloromethylating a fluorobenzene of the formula (I) to obtain a 5-fluorobenzotrichloride of the formula (II), and then reacting it with aqueous ammonia.

The trichloromethylation in the present invention is preferably conducted by adding, preferably dropwise adding, the fluorobenzene of the formula (I) to carbon tetrachloride, preferably to an excess amount of carbon tetrachloride, in the presence of a Lewis acid catalyst, to conduct the reaction. In the present invention, the reaction of the fluorobenzene with carbon tetrachloride is preferably conducted under such a condition that a 5-fluorobenzotrichloride-Lewis acid complex is hardly formed as compared with a carbon tetrachloride-Lewis acid complex, whereby side reactions to form bis-(2,4-dihalogeno-5-fluorophenyl)dichloromethane or bis-(2,3,4-trihalogeno-5-fluorophenyl)dichloromethane can be suppressed, and the desired 5-fluorobenzotrichloride can be obtained in good yield.

The carbon tetrachloride is used usually in an amount of from 2 to 20 moles, preferably from 4 to 10 moles, relative to one mole of the fluorobenzene such as 1,3-dihalogeno-4-fluorobenzene or 1,2,3-trihalogeno-4-fluorobenzene. It is used as a reactant and as a solvent.

As the Lewis acid catalyst, aluminum chloride, aluminum bromide or an aluminum chloride-sodium chloride (1:1) complex may be mentioned. From the industrial point of view, aluminum chloride is preferred. It is used usually in an amount of from 1 to 3 moles, preferably from 1.5 to 2.0 moles per mole of the fluorobenzene.

The reaction temperature is usually from 10° to 80° C., preferably 60° to 80° C. The reaction time is usually from 10 to 60 minutes.

After completion of the reaction, usual post treatment and distillation are conducted to readily obtain the desired 5-fluorobenzotrichloride such as 2,4-dihalogeno-5-fluorobenzotrichloride or 2,3,4-trihalogeno-5-fluorobenzotrichloride. A 5-fluorobenzonitrile can be obtained by reacting the obtained 5-fluorobenzotrichloride with aqueous ammonia.

The concentration of the aqueous ammonia is preferably from 25 to 40%. It is used usually in an amount of from 10 to 40 moles, preferably from 20 to 30 moles, per mole of the 5-fluorobenzotrichloride. The reaction temperature is preferably from 90° to 120° C., and the reaction time is preferably form 5 to 20 hours. After completion of the reaction, the ammonia is recovered, and then the mixture is filtered. The filtrate is distilled to obtain the desired 5-fluorobenzonitrile.

In the present invention, the fluorination of the 5-fluorobenzonitrile is preferably conducted in a solvent or in the absence of a solvent by means of an alkali metal fluoride such as KF, RbF or CsF. Particularly preferred is KF.

A preferred solvent for the reaction is an aprotic polar solvent such as dimethylsulfoxide, dimethylformamide, sulfolane or N-methylpyrrolidone. The fluorination reaction may be conducted in the presence of a phase transfer catalyst. Preferred phase transfer catalysts include ammonium salts or phosphonium salts such as tetramethyl ammonium chloride, tetrabutyl ammonium bromide, tetrabutylphosphonium bromide and tetraphenylphosphonium bromide.

In the 5-fluorobenzonitrile of the formula (III), when each of $X_1$ to $X_3$ is Cl, Br or I, it will be substituted by fluorine, and each of $Y_1$ to $Y_3$ in the corresponding formula (IV) will be F. In this case, the reactivity of $X_1$ to $X_3$ for fluorine substitution is $X_3 > X_1 > X_2$. The reactivity of $X_2$ for fluorine substitution is higher in the case where $X_3 = X_1 =$ halogen atom other than F than the case where $X_3 = X_1 = F$. By the fluorine substitution reaction of $X_1$ to $X_3$, a mixture will be obtained which comprises a compound wherein all of $Y_1$ to $Y_3$ are F and a compound wherein a part of $Y_1$ to $Y_3$ is F.

As the alkali metal fluoride, KF is preferred. Particularly preferred is a material of fine particle form. KF is used usually in an amount of from 1 to 4 molar excess, preferably from 1.2 to 2.5 molar excess, relative to the theoretical amount required for the reaction for mono-, di- or tri- substitution.

The solvent for reaction is used usually in an amount of from 1 to 10 times preferably from 2 to 6 times, the weight of the compound of the formula (III). In a case where a phase transfer catalyst is employed, the amount is selected usually within a range of from 1 to 30 mol %, preferably from 5 to 15 mol %, relative to the material to be fluorinated.

The optimum conditions such as the reaction temperature, time and pressute, may suitably be selected as the conditions for the mono-, di- or tri- substitution fluorination of the present invention. However, such fluorination is conducted usually within a temperature range of from 100° to 220° C. for 1 to 20 hours under a pressure of from 0 to 1.0 kg/cm². The compound of the formula (IV) such as 2-chloro-4,5-difluorobenzonitrile or 2,4,5-trifluorobenzonitrile obtained by the fluorination of the compound of the formula (III) such as 2,4-dichloro-5-fluorobenzonitrile, can be isolated by a usual method for separation such as filtration, distillation, etc.

The hydrolysis of the benzonitrile of the formula (IV) is usually conducted in a water-containing sulfuric acid. The optimum conditions may suitably be selected as the reaction conditions for the hydrolytic reaction of the present invention such as the sulfuric acid concentration, the weight ratio with the benzonitrile, the reaction temperature and time. However, the hydrolysis can usually be conducted at a concentration of from 50 to 70%, at a weight ratio of from 2 to 10, at a temperature of from 100° to 160° C. for a reaction time of from 1 to 12 hours.

The 2-chloro-4,5-difluoro or 2,4,5-trifluorobenzoic acid obtained by the hydrolysis of the benzonitrile such as 2-chloro-4,5-difluoro or 2,4,5-trifluorobenzonitrile, can usually be purified to a high purity by usual post-treatment.

The hydrolysis of the trichloromethyl product of the formula (II), is conducted in water-containing sulfuric acid. The optimum conditions may suitably be selected as the reaction conditions for the hydrolytic reaction of the present invention, such as the sulfuric acid concentration, the weight ratio with trichloromethyl product, the reaction temperature or time. However, the hydrolysis can be conducted usually at a concentration of from 85 to 95%, at a weight ratio of from 1 to 4, at a temperature of from 30 to 100° C. for a reaction time of from 1 to 5 hours.

The 2,4-dihalogeno-5-fluorobenzoic acid obtained by the hydrolysis of the 2,4-dihalogeno-5-fluorobenzotrichloride of the formula (II), or the 2,3,4-trihalogeno-5-fluorobenzoic acid obtained by the hydrolysis of the 2,3,4-trihalogeno-5-fluorobenzotrichloride of the formula (II), can be obtained in a high purity and in good yield by usual post-treatment and filtration.

2,4-dichloro-5-fluorobenzonitrile and 2-chloro-4,5-difluorobenzonitrile in the compounds of the formula (III), and 2-chloro-4,5-difluorobenzotrichloride and 2,4,5-trifluorobenzotrichloride in the compounds of the formula (II), are novel substances identified for the first time by the present invention.

Now, the present invention will be described in further detail with reference to Examples. However, it should be understood that the present invention is by no means restricted by such specific Examples.

EXAMPLE 1

Into a 200 ml four-necked flask equipped with a stirrer, a reflux condenser, a thermometer and a dropping funnel, 97 ml (1 mol) of carbon tetrachloride and 33.3 g (0.25 mol) of aluminum chloride were charged, and 16.5 g (0.1 mol) of 1,3-dichloro-4-fluorobenzene was dropwise added thereto at 75° C. Thereafter, the mixture was reacted for 10 minutes. After cooling, the reaction mixture was poured into 300 ml of ice water, and the organic layer was washed with a 5% sodium hydrogen carbonate aqueous solution. The organic layer thereby obtained was analyzed by gas chromatography and was found to be a carbon tetrachloride solution comprising a trichloromethyl product (70%) and bis(2,4-dichloro-5-fluorophenyl)dichloromethane (30%).

After distilling off carbon tetrachloride, the residue was cooled, whereby crystals precipitated partially. The crystals were removed by filtration to obtain 21.3 g of crude oil. Then, this crude oil and 146 g (3 mol) of 35% aqueous ammonia were charged into a 500 ml pressure reactor and reacted at a temperature of from 103° to 106° C. for 12 hours.

After completion of the reaction, ammonia was distilled off, and the crystalline product was collected by filtration and washed with.10 ml of chloroform. The filtrate and the chloroform washing solution were subjected to liquid separation, and the aqueous layer was extracted with chloroform. The extract was put together with the separated organic layer, followed by washing with water and drying. After distilling off chloroform, the residue was distilled under reduced pressure to obtain 10.6 g (yield: 55.8%) of 2,4-dichloro-5-fluorobenzonitrile. Boiling point: 93°-95° C./1 mmHg; melting point: 43°-44° C.

This product was analyzed by the following analyses to identify the structure.

IR analysis (KBr) (cm$^{-1}$); 3070, 2210, 1570, 1465.

NMR analysis $<^1$Hnmr$>$ δppm from TMS in CDCl$_3$; δ7.48 (1H, d, J=8.2 Hz); δ7.61 (1H, d, J=6.7 Hz).

Elementary analysis Analyzed value: Cl 37.3%; Calculated value as C$_7$H$_2$Cl$_2$FN: Cl 37.32%.

EXAMPLE 2

A mixture comprising 5.70 g (0.03) of 2,4-dichloro-5-fluorobenzonitrile, 3.48 g (0.06 mol) of spray dried KF and 30 ml of dimethylsulfoxide, was reacted at a temperature of from 140° to 150° C. for 3.5 hours in a glass reactor. After completion of the reaction, the mixture was poured into ice water (50 ml) and extracted with chloroform. The chloroform extract was washed five times with water and then dried. Then chloroform was distilled off. The residue was distilled under reduced pressure to obtain 3.57 g (yield: 68.6%) of 2-chloro-4,5-difluorobenzonitrile. Boiling point: 105°-107° C./37 mmHg; melting point: 35°-37° C.

This product was analyzed by the following analyses to confirm its structure. IR analysis (KBr) (cm$^{-1}$); 3050, 2220, 1590, 1500.

MNR analysis $<^{19}$Fnmr$>$ δppm from CFCl$_3$ in (CD$_3$)$_2$CO; δ−125.7 ppm (d,d,d, J$_{F-F}$=20.6 Hz, J$_{F-H}$=9.9 Hz, J$_{F-H}$=7.9 Hz); δ−136.8 ppm (d,d,d, J$_{F-F}$=20.6 Hz, J$_{F-H}$=9.8 Hz, J$_{F-H}$=7.0 Hz); $<^1$Hnmr$>$ δppm from TMS in (CD$_3$)$_2$CO; δ7.78 ppm (1H,d,d, J$_{F-H}$=9.9 Hz, J$_{F-H}$=7.9 Hz); δ8.00 ppm (1H,d,d, J$_{F-H}$=9.8 Hz, J$_{F-H}$=7.9 Hz).

Elementary analysis Analyzed value: Cl 20.4%; Calculated value as C$_7$H$_2$ClF$_2$N: Cl 20.43%.

2.10 g of the 2-chloro-4,5-difluorobenzonitrile obtained as above and 12 ml of 60% sulfuric acid were reacted under reflux for 10 hour. After cooling, the mixture was diluted with 20 ml of water and then extracted with chloroform (10 ml×2 times). The extract was washed with water and dried, and then the solvent was distilled off to obtain 2.20 g (yield: 94.8%) of 2-chloro-4,5-difluorobenzoic chloro-4,5-difluorobenzoic acid. Melting point: 103°-105° C.

EXAMPLE 3

A mixture comprising 9.50 g (0.05 mol) of 2,4-dichloro-5-fluorobenzonitrile, 14.5 g (0.25 mol) of spray dried KF and 35 ml of dimethylsulfoxide, was reacted at a temperature of from 160° to 165° C. for 5 hours in a glass reactor. After completion of the reaction, inorganic substances were collected by filtration and washed with chloroform. The filtrate and the washing solution were poured into water and extracted with chloroform. Then, the extract was washed with water and dried. Then, chloroform was distilled off. The residue was distilled under reduced pressure to obtain 3.36 g (yield: 42.8%) of 2,4,5-trifluorobenzonitrile. Boiling point: 94°-95° C./50 mmHg, $n_D^{20}$1.473.

1.57 g of the 2,4-trifluorobenzonitrile obtained as above and 10 ml of 60% sulfuric acid were refluxed for 9 hours. After cooling, the reaction mixture was poured into water and extracted with chloroform. The extract solution was washed with water and dried. The solvent was distilled off to obtain 1.58 g (yield: 90%) of 2,4,5-trifluorobenzoic acid. Melting point: 93°-95° C.

EXAMPLE 4

Into a 200 ml four-necked flask equipped with a stirrer, a reflux condenser, a thermometer and a dropping funnel, 97 ml (1 mol) of carbon tetrachloride and 26.7 g (0.2 mol) of aluminum chloride were charged, and 14.9 g (0.1 mol) of 1-chloro-3,4-difluorobenzene was gradually dropwise added over a period of 1.5 hours under reflux so that hydrochloride gas was slowly generated. The generated hydrochloride gas was absorbed by an aqueous sodium hydroxide solution. After completion of the dropwise addition, the mixture was reacted for 10 minutes. After cooling to room temperature, the reaction mixture was poured into 300 ml of ice water. The organic layer was separated and washed with 100 ml of water, then with 100 ml of 5% of sodium hydrogen carbonate aqueous solution and further with 100 ml of water. After distilling off carbon tetrachloride, the residue was distilled under reduced pressure to obtain 17.4 g (yield: 65.4%) of 2-chloro-4,5-difluorobenzotrichloride. Boiling point: 104°-106° C./8 mmHg, $n_D^{20}$1.540; purity: 98.2%

This product was analyzed by the following analyses to confirm its structure.

IR analysis (neat) (cm$^{-1}$); 3060, 1601, 1485, 765 (CCl$_3$).

NMR analysis <$^{19}$Fnmr>δppm from CFCl$_3$ in (CD$_3$)$_2$CO; δ132.5 ppm (d,d,d, $J_{F-F}$=20.6 Hz, $J_{F-H}$=11.9 Hz, $J_{F-H}$=20.6 Hz); δ137.5 ppm (d,d,d, $J_{F-F}$=20.6 Hz, $J_{F-n}$=11.9 Hz, $J_{F-H}$=7.3 Hz); <$^1$Hnmr>δppm from TMS in (CD$_3$)$_2$CO; δ7.70 ppm (1H, d,d, $J_{H-F}$=9.9 Hz, $J_{H-F}$=7.3 Hz); δb 8.21 ppm (1H, d,d, $J_{H-F}$=11.9 Hz, $J_{H-F}$=8.1 Hz).

Elementary analysis Analyzed value: Cl 53.4%; Calculated value as C$_7$H$_2$Cl$_4$F$_2$ Cl 53.33%.

Then, into a 100 ml four-necked flask equipped with a stirrer, a reflux condenser, a thermometer and a dropping funnel, 47 g of 95% sulfuric acid was charged, and 17.4 g of 2-chloro-4,5-difluorobenzotrichloride was dropwise added thereto at a temperature of from 40° to 45° C. Hydrochloride gas generated was absorbed by an aqueous sodium hydroxide solution. After reacting the mixture for one hour, the mixture was poured into 300 ml of ice water, and precipitated crystals were collected by filtration. The crystals were washed with a small amount of cool water and dried to obtain 12.1 g (yield: 96%) of 2-chloro-4,5-difluorobenzoic acid. Melting point: 103°-105° C.

EXAMPLE 5

The reaction and the post treatment were conducted in the same manner as in Example 4 except that 38.3 g of a pulverized product of a fused mixture of aluminum chloride-sodium chloride (1:1) was used instead of 26.7 g of aluminum chloride, to obtain 14.1 g of (yield: 53%) of 2-chloro-4,5-difluorobenzotrichloride.

EXAMPLE 6

Into a 200 ml four-necked flask equipped with a stirrer, a reflux condenser, a thermometer and a dropping funnel, 97 ml (1 mol) of carbon tetrachloride and 26.7 g (0.2 mol) of aluminum chloride were charged, and 16.5 g (0.1 mol) of 1,3-dichloro-4-fluorobenzene was dropwised added thereto under reflux. Thereafter, the mixture was reacted for 20 minutes. Post treatment was conducted in the same manner as in Example 4 to obtain 17.7 g (yield: 62.6%) of 2.4-dichloro-5-fluorobenzotrichloride.

Boiling point: 94°-95° C./1mmHg; $n_D^{20}$1.577; purity: 98.1%.

This product was analyzed was the following analyses to confirm its structure.

IR analysis (neat) (cm$^{-1}$); 3070, 1570, 1455, 767 (CCl$_3$).

NMR analysis <$^{19}$Fnmr>δppm from CFCl$_3$ in (CD$_3$)$_2$CO; δ−115.5 ppm (d,d, $J_{F-H}$=10.3 Hz, $J_{F-H}$=6.8 Hz); <$^1$Hnmr>δpm from TMS in (CD$_3$)$_2$CO; δ7.58 ppm (1H, d, J=6.8 Hz); δ7.99 ppm (1H, d, H=10.3 Hz).

Elementary analysis Analyzed value: Cl 62.7% Calculated value as C$_7$H$_2$Cl$_5$F: Cl$_{62.78}$%.

Then, in the same manner as in Example 4, 17.7 g of 2,4-dichloro-5-fluorobenzotrichloride was dropwise added to 40 g of 95% sulfuric acid at 40° C. to conduct the hydrolysis, and treatment was conducted in the same manner to obtain 12.7 g (yield: 97%) of 2,4-dichloro-5-fluorobenzoic acid. Melting point 141°-142° C.

EXAMPLE 7

Into a 200 ml four-necked flask equipped with a stirrer, a reflux condenser, a thermometer and a dropping funnel, 97 ml (1 mol) carbon tetrachloride and 26.7 g (0.2 mol) of aluminum chloride were charged, and 13.2 g (0.1 mol) of 1,3,4-trifluorobenzene was dropwise added thereto under reflux. Thereafter, the mixture was reacted for 20 minutes. The reaction mixture was treated in the same as in Example 1 to obtain 7.49 g of (yield: 30%) of 2,4,5-trifluorobentrichloride.

Boiling point: 93°-95° C/1mmHg; $n_D^{20}$1.506; purity: 98.3%.

This product was analysed by the following analyses to confirm its structure.

IR analysis (neat) (cm$^{-1}$); 3060, 1620, 1505, 767 (CCl$_3$).

NMR analysis <$^{19}$Fnmr>δppm from CFCl$_3$ in (CD$_3$)$_2$CO; δ−115.5 ppm (d,d,d, $J_{F-F}$=20.6 Hz, $J_{F-H}$=10.8 Hz, $J_{F-H}$=6.7 Hz); δ−129.5 ppm (d,d,d,d, $J_{F-F}$=20.6 Hz, $J_{F-F}$=10.8 Hz, $J_{F-H}$=10.8 Hz, $J_{F-H}$=7.9 Hz); δ−141.7 ppm (d,d,d, $J_{F-F}$=20.6 Hz, $J_{F-H}$=10.8 Hz, $J_{F-H}$=7.9 Hz); <$^1$Hnmr>δppm from TMS in (CD$_3$)$_2$CO; δ7.49 ppm (1H, d,d,d, $J_{H-F}$=10.5 Hz, $J_{H-F}$=10.5 Hz, $J_{H-F}$=6.7 Hz); δ7.99 ppm (1H, d,d,d, $J_{H-F}$=10.8 Hz, $J_{H-F}$=7.9 Hz, $J_{H-F}$=7.9 Hz).

Elementary analysis Analyzed value: Cl 42.4%; Calculated value as C$_7$H$_2$Cl$_3$F$_3$:Cl 42.64%.

Then, in the same manner as in Example 4, 7.46 g of 2,4,5-trifluorobenzotrichloride was dropwise added to 30 g of 95% sulfuric acid at 40° C to conduct hydrolysis, and treatment was conducted in the same manner to obtain 5.0 g (yield: 94.6%) of 2,4,5-trifluorobenzoic acid. Melting point 95°-96° C.

EXAMPLE 8

Into a 200 ml four-necked flask equipped with a stirrer, a reflux condenser, a thermometer and a dropping funnel, 97 ml (1 mol) of carbon tetrachloride and 26.7 g (0.2 mol) of aluminum chloride were charged, and 19.3 g (0.1 mol) of 1-bromo-3,4-difluorobenzene was dropwise added under reflux. Thereafter, the mixture was reacted for 30 minutes. The reaction mixture was treated in the same manner as in Example 1 to obtain 21.1 g (yield: 68.1%) of 2-bromo-4,5-difluorobenzotrichloride.

Boiling point: 96°–98° C./1 mmHg; $n_D^{20}$ 1.563; purity: 98.6%.

This product was analysed by the following analyses to confirm its structure.

IR analysis (neat) (cm$^{-1}$) 3050, 1600, 1480, 760 (CCl$_3$).

NMR analysis <19Fnmr>δppm from CFCl$_3$ in (CD$_3$)$_2$CO; δ−133.0 ppm (d,d,d, $J_{F-F}$=21.2 Hz, $J_{F-H}$=9.1 Hz, $J_{F-H}$=7.4 Hz); δ−136.9 ppm (d,d,d, $J_{F-F}$=21.6 Hz, $J_{F-H}$=11.4 Hz, $J_{H-F}H$=7.1 Hz); <1Hnmr>δppm from TMS in (CD$_3$)$_2$CO; δ7.90 ppm (1H, d,d, $J_{H-F}$=11.4 Hz, $J_{H-F}$=7.4 Hz); δ8.27 ppm (1H, d,d, $J_{H-F}$=9.1 Hz, $J_{H-F}$=7.1 Hz).

Elementary analysis Analyzed value: Cl 34.3%; Calculated value as C$_7$H$_2$BrCl$_3$F$_2$:Cl 34.27%.

Then, in the same manner as in Example 4, 17.5 g of 2-bromo-4,5-difluorobenzotrichloride was dropwise added to 50 g of 95% sulfuric acid at 40° C., and the hydrolysis was conducted for two hours and treatment was conducted in the same manner to obtain 12.6 g (yield: 94%) of 2-bromo-4,5-difluorobenzoic acid. Melting point 110.5°–11.5° C.

EXAMPLE 9

Into a 200 ml four-necked flask equipped with a stirrer, a reflux condenser, a thermometer and a dropping funnel, 97 ml (1 mol) of carbon tetrachloride and 26.7 g (0.2 mol) of aluminum chloride were charged, and 20.0 g (0.1 mol) of 1,2,3-trichloro-4-fluorobenzene was dropwise added under reflux. Thereafter, the mixture was reacted for 30 minutes. The reaction mixture was treated in the same manner as in Example 1 to obtain 19.9 g (yield: 62.8%) of 2,3,4-trichloro-5-fluorobenzotrichloride.

Melting point: 72°–73° C.; purity: 98.7%.

This product was analysed by the following analyses to confirm its structure.

IR analysis (neat) (cm$^{-1}$); 3060, 1590, 1470, 765 (CCl$_3$).

NMR analysis <$^{19}$Fnmr>δppm from CFCl$_3$ in (CD$_3$)$_2$CO; δ−115.0 ppm (d, $J_{F-H}$=8.8 Hz); <1Hnmr>δppm from TMS in (CD$_3$)$_2$CO; δ7.77 ppm (d, $J_{H-F}$=8.8Hz).

Elementary analysis Analyzed value: Cl 67.2%; Calculated value as C$_7$HCl$_6$F: Cl 67.19%.

Then, in the same manner as in Example 4, 19.9 g of 2,3,4-trichloro-5-fluorobenzotrichloride was dropwise added to 50 g of 95% sulfuric acid at 40° C., and the hydrolysis was conducted for two hours and treatment was conducted in the same manner to obtain 14.5 g (yield: 95%) of 2,3,4-trichloro-5-trifluorobenzoic acid.

Melting point 150.0°–151° C.

As described in the foregoing, according to the present invention, fluorobenzonitriles, fluorobenzotrichlorides and fluorobenzoic acids useful as intermediates for medicines can be prepared safely and simply on an industrial scale from fluorobenzenes.

We claim:

1. A process for producing a 5-fluorobenzoic acid of the formula (V), which comprises trichloromethylating a fluorobenzene of the formula (I) to obtain a 5-fluorobenzotrichloride of the formula (II), then reacting it with aqueous ammonia to obtain a 5-fluorobenzonitrile of the formula (III), reacting it with a fluorinating agent to obtain a 5-fluorobenzonitrile of the formula (IV) and hydrolyzing it:

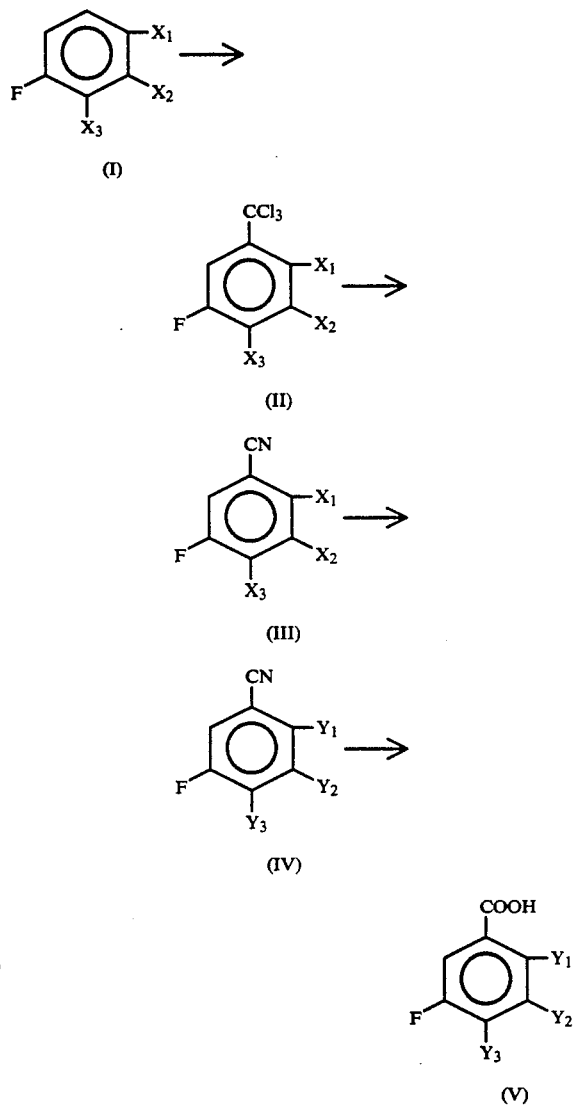

wherein each of $X_1$, $X_3$, $Y_1$ and $Y_3$ is a halogen atom, and each of $X_2$ and $Y_2$ is hydrogen or a halogen atom, with the proviso that at least one of $X_1$, $X_2$ and $X_3$ is a halogen atom other than fluorine, wherein said step of reacting the compound of formula (III) with a fluorinating agent converts at least one of said halogen atom other than fluorine to fluorine at the corresponding ring position of $Y_1$, $Y_2$ and $Y_3$.

2. A process for producing a 5-fluorobenzoic acid of the formula (VI), which comprises reacting a fluorobenzene of the formula (I) with carbon tetrachloride in the presence of a Lewis acid catalyst to obtain a 5- fluorobenzotrichloride of the formula (II), and hydrolyzing it:
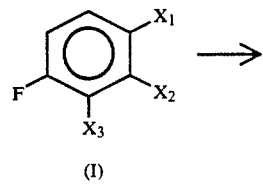
(I)
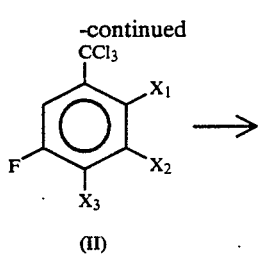
(II)
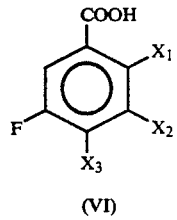
(VI)
wherein each of $X_1$ and $X_3$ is a halogen atom, and $X_2$ is hydrogen or a halogen atom.
* * * * *